United States Patent [19]

Clark

[11] Patent Number: 5,770,592
[45] Date of Patent: Jun. 23, 1998

[54] PREVENTION AND TREATMENT OF OCULAR NEOVASCULARIZATION USING ANGIOSTATIC STEROIDS

[75] Inventor: Abbot F. Clark, Arlington, Tex.

[73] Assignee: Alcon Laboratories, Inc., Fort Worth, Tex.

[21] Appl. No.: 895,184

[22] Filed: Jul. 16, 1997

Related U.S. Application Data

[63] Continuation of Ser. No. 342,524, Nov. 21, 1994, Pat. No. 5,679,666, and Ser. No. 796,169, Nov. 22, 1991, abandoned.

[51] Int. Cl.$^6$ .................................................. A61K 31/33
[52] U.S. Cl. ........................ 514/179; 514/180; 514/181; 514/182; 514/912
[58] Field of Search .................................. 514/179, 180, 514/181, 182, 912

[56] References Cited

U.S. PATENT DOCUMENTS

| | | | |
|---|---|---|---|
| 4,771,042 | 9/1988 | Braughler et al. | 514/171 |
| 4,876,250 | 10/1989 | Clark | 514/179 |
| 4,975,537 | 12/1990 | Aristoff et al. | 540/9 |

FOREIGN PATENT DOCUMENTS

WO 91/19731   10/1990   WIPO .

OTHER PUBLICATIONS

Crum, et al., "A New Class of Steriods Inhibits Angiogenesis in the Presence of Heparin or Heparin Fragment," *Science*, 230 pp. 375–378 (Dec. 20, 1985).

Ingber, et al., "A Possible Mechanism of Inhibition of Angiogenesis by Angiostatic Steroids: Induction of Capillary Basement Membrane Dissolution," *Endocrinology* 119, pp. 768–775 (1986).

Li, et al., "Angiostatic Steroids Potentiated by Sulphated Cyclodextrin Inhibit Corneal Neovascularization," *Investigative Ophthalmology and Visual Science*, vol. 32, No. 11, pp. 2898–2905 (Oct., 1991).

Folkman, et al., "Angiogenic Factors," *Science*, vol. 235, pp. 442–447 (1987).

Furcht, "Critical Factors Controlling Angiogenesis: Cell Products, Cell Matrix, and Growth Factors," *Laboratory Investigation*, vol. 55, No. 5, pp. 505–509 (1986).

Cariou, et al., "Inhibition of Human Endothelial Cell Proliferation by Heparin and Steroids," *Cell Biology International Reports*, vol. 12, No. 12, pp. 1037–1047 (Dec., 1988).

Tokida, et al., "Production of Two Variant Laminin Forms by Endothelial Cells and Shift of Their Relative Levels by Angiostatic Steroids," *The Journal of Biological Chemistry*, vol. 264, No. 30, pp. 18123–18129 (Oct. 25, 1990).

Maragoudakis, et al., "Antiangiogenic Action of Heparin Plus Cortisone is Associated with Decreased Collagenous Protein Synthesis in the Chick Chorioallantoic Membrane System," *The J. of Pharm. and Experimental Therapeutics*, vol. 251(22), pp. 679–682 (1989).

Ashino–Fuse, et al., "Medroxyprogesterone Acetate, An Anti–Cancer and Anti–Angiogenic Steroid, Inhibits the Plasminogen Activator in Bovine Endothelial Cells," *Int. J. Cancer*, 44, pp. 859–864 (1989).

BenEzra "Neovasculogenic Ability of Prostaglandins, Growth Factors, and Synthetic Chemoattractants," *American Journal of Ophthalmology*, vol. 86, No. 4, pp. 455–461 (Oct., 1978).

*Primary Examiner*—Zohreh Fay
*Attorney, Agent, or Firm*—Sally Yeager

[57] ABSTRACT

Methods and formulations for treating ocular neovascularization using angiostatic steroids are disclosed.

5 Claims, 1 Drawing Sheet

PREVENTION AND TREATMENT OF OCULAR NEOVASCULARIZATION USING ANGIOSTATIC STEROIDS

This application is a continuation of U.S. Ser. No. 08/342,524 filed on Nov. 21, 1994, now U.S. Pat. No. 5,679,666, and a continuation of U.S. Ser. No. 07/796,169, filed on Nov.22, 1991, now abondoned.

FIELD OF THE INVENTION

This invention relates to the use of angiostatic steroids in preventing and treating ocular neovascularization.

DESCRIPTION OF THE RELATED ART

Steroids functioning to inhibit angiogenesis in the presence of heparin or specific heparin fragments are disclosed in Crum, et al., *A New Class of Steroids Inhibits Angiogenesis In The Presence of Heparin or Heparin Fragment*, Science, 230, pp. 375–378 (Dec. 20, 1985). The authors refer to such steroids as "angiostatic" steroids. Included in the new class of steroids found to be angiostatic are cortisol, cortexolone, and several dihydro and tetrahydro derivatives. In a follow up study directed to testing a hypothesis as to the mechanism by which the steroids inhibit angiogenesis, it was shown that heparin/angiostatic steroid compositions caused dissolution of the basement membrane scaffolding to which anchorage dependent endothelia are attached resulting in capillary involution; see, Ingber, et al. *A Possible Mechanism for Inhibition of Angiogenesis by Angiostatic Steroids: Induction of Capillary Basement Membrane Dissolution*, Endocrinology 119, pp. 768–775 (1986).

A group of tetrahydrosteroids useful in inhibiting angiogenesis is disclosed in U.S. Pat. No. 4,975,537, issued to Aristoff, et al. The compounds are disclosed for use in treating head trauma, spinal trauma, septic or traumatic shock, stroke, and hemorrhage shock. In addition, the patent discusses the utility of these compounds in embryo implantation and in the treatment of cancer, arthritis, and arteriosclerosis. The compounds are not disclosed for ophthalmic use. Some of the tetrahydrosteroids disclosed in Aristoff, et al. are disclosed in U.S. Pat. No. 4,771,042 in combination with heparin or a heparin fragment for inhibiting angiogenesis in a warm blooded animal. The patent does not disclose the combination for ophthalmic use.

Compositions of hydrocortisone, "tetrahydrocortisol-S," and U-72, 745G, each in combination with a beta cyclodextrin have been shown to inhibit corneal neovascularization. Li, et al., *Angiostatic Steroids Potentiated by Sulphated Cyclodextrin Inhibit Corneal Neovascularization*, Investigative Ophthalmology and Visual Science, Vol. 32, No. 11, pp. 2898–2905(October, 1991). The steroids alone reduce neovascularization somewhat but are not effective alone in providing for regression of neovascularization.

SUMMARY OF THE INVENTION

This invention is directed to methods for preventing and treating ocular neovascularization with particular angiostatic steroids. The angiostatic steroids are useful in not only preventing neovascularization, but will also provide for regression of neovascularization.

DETAILED DESCRIPTION OF THE PREFERRED EMBODIMENTS

Figure 1:
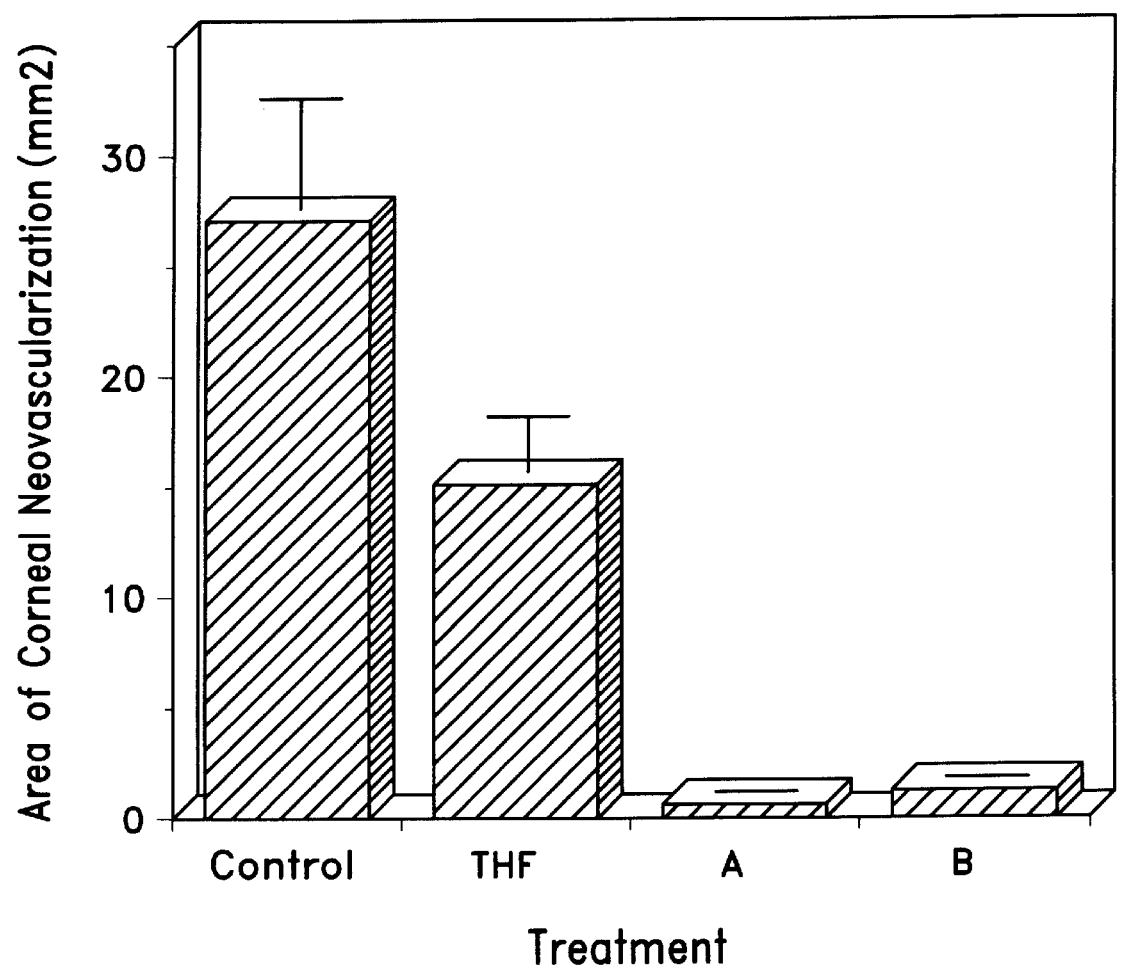
FIG. 1—Compares the ability of angiostatic steroids to inhibit neovascularization in the rabbit cornea.

The development of blood vessels for the purpose of sustaining vital tissue is known as angiogenesis or neovascularization. Agents which inhibit neovascularization are known by a variety of terms such as angiostatic, angiolytic, or angiotropic agents. For purposes of this specification, the term "angiostatic agent" means compounds which can be used to inhibit neovascularization.

Ocular neovascularization has not been successfully treated in the past. Neovascularization of tissues in the front of the eye (i.e. the cornea, iris, and the trabecular meshwork) and other conditions, including conditions in the back of the eye, for example, retinal, subretinal, macular, and optical nerve head neovascularization, can be prevented and treated by administration of the steroids of this invention. The angiostatic agents are useful in preventing and treating ocular neovascularization, including providing for the regression of neovascularization.

The angiostatic agents of this invention are steroids available from Steraloids, Inc., Wilton, N. H. and have the following structures and names:

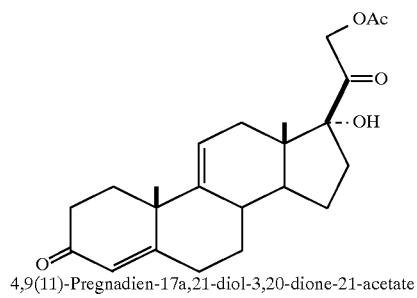

4,9(11)-Pregnadien-17a,21-diol-3,20-dione-21-acetate

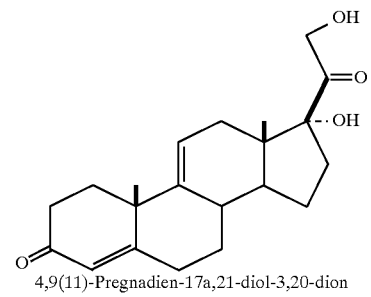

4,9(11)-Pregnadien-17a,21-diol-3,20-dion

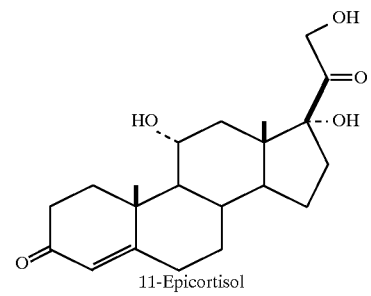

11-Epicortisol

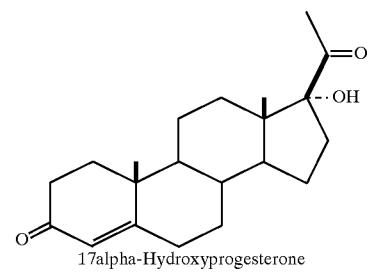

17alpha-Hydroxyprogesterone

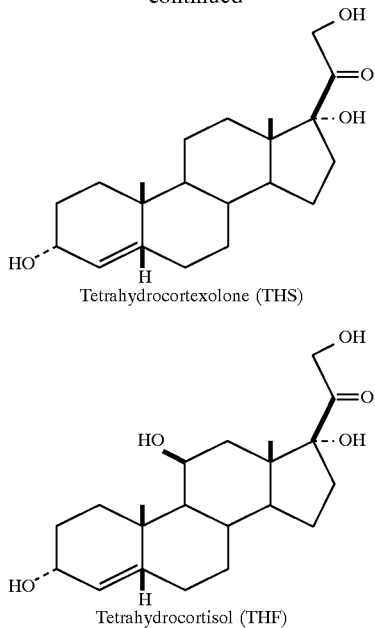

Tetrahydrocortexolone (THS)

Tetrahydrocortisol (THF)

The above structures include all pharmaceutically acceptable salts of the angiostatic steroids.

The preferred angiostatic steroid is 4,9(11)-Pregnadien-17a,21-diol-3,20-dione and its acetate. When treating neovascularization in the back of the eye, for example, in the retina, macula, and optic nerve head, the free alcohol is more preferred.

The angiostatic steroids are useful in preventing and treating any ocular neovascularization, including, but not limited to: retinal diseases (diabetic retinopathy, chronic glaucoma, retinal detachment, sickle cell retinopathy, senile macular degeneration due to subretinal neovascularization); rubeosis iritis; inflammatory diseases; chronic uveitis; neoplasms (retinoblastoma, pseudoglioma); Fuchs' heterochromic iridocyclitis; neovascular glaucoma; corneal neovascularization (inflammatory, transplantation, developmental hypoplasia of the iris); neovascularization resulting following a combined vitrectomy and lensectomy; vascular diseases (retinal ischemia, choroidal vascular insufficiency, choroidal thrombosis, carotid artery ischemia); neovascularization of the optic nerve; and neovascularization due to penetration of the eye or contusive ocular injury.

The initiation of new blood vessel formation may arise quite differently in various tissues or as a result of different diseases. Many substances have been found to induce neovascularization, see, Folkman, et al., *Angiogenic Factors*, Science, Volume 235, pp. 442–447(1987). However, it is believed, that once initiated, the process of neovascularization is similar in all tissues and regardless of the associated disease, Furcht, *Critical Factors Controlling Angiogenesis: Cell Products, Cell Matrix, and Growth Factors*, Laboratory Investigation, Volume 55, No. 5, pp. 505–509 (1986).

There are a variety of theories regarding the mechanism of action of angiostatic steroids. For example, angiostatic steroid induced inhibition of neovascularization may occur due to, dissolution of the capillary basement membrane, Ingber, et al., Supra; inhibition of vascular endothelial cell proliferation, Cariou, et al., *Inhibition of Human Endothelial Cell Proliferation by Heparin and Steroids*, Cell Biology International Reports, Vol. 12, No. 12, pp. 1037–1047 (December, 1988); effect on vascular endothelial cell laminin expression, Tokida, et al., *Production of Two Variant Laminin Forms by Endothelial Cells and Shift of Their Relative Levels* by Angiostatic Steroids, The Journal of Biological Chemistry, Vol. 264, No. 30, pp. 18123–18129 (Oct. 25, 1990); inhibition of vascular cell collagen synthesis, Maragoudakis, et al., *Antiangiogenic Action of Heparin Plus Cortisone is Associated with Decreased Collagenous Protein Synthesis in the Chick Chorioallantoic Membrane System*, The Journal of Pharmacology and Experimental Therapeutics, Vol. 251, No. 2, pp. 679–682 (1989); and inhibition of vascular endothelial cell plasminogen activator activity, Ashino-Fuse, et al., *Medroxyprogesterone Acetate, An Anti-Cancer and Anti-Angiogenic Steroid, Inhibits the Plasminogen Activator in Bovine Endothelial Cells*, Int. J. Cancer, 44, pp. 859–864 (1989).

There are many theories associated with the cause of neovascularization, and there may be different inducers depending on the disease or surgery involved, BenEzra, *Neovasculogenic Ability of Prostaglandins, Growth Factors, and Synthetic Chemoattractants*, American Journal of Ophthalmology, Volume 86, No. 4, pp. 455–461, (October, 1978). Regardless of the cause or the associated disease or surgery, it is believed that angiostatic agents work by inhibiting one or more steps in the process of neovascularization. Therefore, the angiostatic steroids of this invention are useful in the treatment and prevention of neovascularization associated with a variety of diseases and surgical complications.

The angiostatic steroids of the present invention may be incorporated in various formulations for delivery to the eye. For example, topical formulations can be used and can include ophthalmologically acceptable preservatives, surfactants, viscosity enhancers, buffers, sodium chloride, and water to form aqueous sterile ophthalmic solutions and suspensions. In order to prepare sterile ophthalmic ointment formulations, an angiostatic steroid is combined with a preservative in an appropriate vehicle, such as mineral oil, liquid lanolin, or white petrolatum. Sterile ophthalmic gel formulations comprising the angiostatic steroids of the present invention can be prepared by suspending an angiostatic steroid in a hydrophilic base prepared from a combination of, for example, Carbachol-940(a carboxy vinyl polymer available from the BF Goodrich Company) according to published formulations for analogous ophthalmic preparations. Preservatives and antimicrobial agents may also be incorporated in such gel formulations. Systemic formulations, for example, orally ingested tablets and formulations for intraocular injection are also contemplated.

The specific type of formulation selected will depend on various factors, such as the angiostatic steroid or its salt being used, the dosage frequency, and the location of the neovascularization being treated. Topical ophthalmic aqueous solutions, suspensions, ointments, and gels are the preferred dosage forms for the treatment of neovascularization in the front of the eye (the cornea, iris, trabecular meshwork); or neovascularization of the back of the eye if the angiostatic agent can be formulated such that it can be delivered topically and the agent is able to penetrate the tissues in the front of the eye. The angiostatic steroid will normally be contained in these formulations in an amount from about 0.01 to about 10.0 weight/percent. Preferable concentrations range from about 0.1 to about 5.0 weight/percent. Thus, for topical administration, these formulations are delivered to the surface of the eye one to six times a day, depending on the routine discretion of the skilled clinician.

Systemic administration, for example, in the form of tablets is useful for the treatment of neovascularization particularly of the back of the eye, for example, the retina. Tablets containing 10–100 mg of angiostatic agent can be taken 2–3 times per day depending on the discretion of the skilled clinician.

The following examples illustrate formulations of the present invention, but are in no way limiting.

EXAMPLE 1

| Ingredient | Amount (wt. %) |
|---|---|
| 4,9(11)-Pregnadien-17a,21-diol-3,20-dione-21-acetate | 1.0 |
| Tyloxapol | 0.01 to 0.05 |
| HPMC | 0.5 |
| Benzalkonium chloride | 0.01 |
| Sodium chloride | 0.8 |
| Edetate Disodium | 0.01 |
| NaOH/HCl | q.s. pH 7.4 |
| Purified Water | q.s. 100 mL |

The formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

The 4,9(11)-Pregnadien-17a,21-diol-3,20-dione-21-acetate is sterilized by either dry heat or ethylene oxide. If ethylene oxide sterilization is selected, aeration for at least 72 hours at 50° C. is necessary. The sterilized 4,9(11)-Pregnadien-17a,21-diol-3,20-dione-21-acetate is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl. The formulation will be given topically, in a therapeutically effective amount. In this instance, the phrase "therapeutically effective amount" means an amount which is sufficient to substantially prevent or reverse any ocular neovascularization. The dosage regimen used will depend on the nature of the neovascularization, as well as various other factors such as the patient's age, sex, weight, and medical history.

EXAMPLE 2

Tablet:
5–100 mg 4,9(11)-Pregnadien-17a,21-diol-3,20-dione-21-acetate with inactive ingredients such as starch, lactose and magnesium stearate can be formulated according to procedures known to those skilled in the art of tablet formulation.

EXAMPLE 3

Formulation for Sterile Intraocular Injection each mL contains:

| | |
|---|---|
| 4,9(11)-Pregnadien-17a,21-diol-3,20-dione | 10–100 mg |
| Sodium Chloride | 7.14 mg |
| Potassium Chloride | 0.38 mg |
| Calcium chloride dihydrate | 0.154 mg |
| Magnesium chloride hexahydrate | 0.2 mg |
| Dried sodium phosphate | 0.42 mg |
| Sodium bicarbonate | 2.1 mg |
| Dextrose | 0.92 mg |
| Hydrochloric acid or sodium hydroxide to adjust pH to approximately 7.2 | |
| Water for injection | |

EXAMPLE 4

Inhibition of angiogenesis in the rabbit corneal neovascularization model:

The corneal pocket system of BenEzra (Am. J. Ophthalmol 86:455–461, 1978) was used to induce corneal neovascularization in the rabbit. A small Elvax pellet containing 0.5 $\mu$g of lipopolysaccharide (LPS) was inserted into the middle of the corneal stroma and positioned 2.5 mm from the limbus. An additional Elvax pellet with or without 50$\mu$g of angiostatic steroid was placed next to the LPS implant. The eyes were examined daily and the area of neovascularization calculated. Results after 8 days of LPS implantation are shown in FIG. 1. THF—tetrahydrocortisol; A=4,9(11)-Pregnadien-17a,21-diol3,20-dione-21-acetate; B=4,9(11)-Pregnadien-17a,21-diol-3,20-dione. As can be seen, A & B totally inhibited corneal neovascularization, whereas THF partially inhibited the neovascular response.

I claim:

1. A method for preventing and treating the ocular neovascularization associated with conditions or diseases selected from the group consisting of diabetic retinopathy, chronic glaucoma, retinal detachment, sickle cell retinopathy, senile macular degeneration, rubeosis iritis, uveitis, neoplasms, Fuchs' heterochromic iridocyclitis, neovascular glaucoma, corneal neovascularization, neovascularization resulting from combined vitrectomy and lensectomy, retinal ischemia, choroidal vascular insufficiency, choroidal thrombosis, carotid artery ischemia, and contusive ocular injury, which comprises: administering, topically, systemically, or intraocularly, to a host in need thereof, a pharmaceutically effective amount of an angiostatic steroid selected from the group consisting of: 4,9(11)-Pregnadien-17a,21-diol3,20-dione,11-Epicortisol, 17 alpha-Hydroxprogesterone, and Tetrahydrocortexolone (THS).

2. The method of claim 1 wherein the angiostatic steroid is 4,9(11)-Pregnadien-17a, 21-diol-3,20-dione-21-acetate.

3. The method of claim 1 wherein the angiostatic steroid is 4,9(11)-Pregnadien-17a, 21-diol-3,20-dione.

4. The method of claim 1 wherein the angiostatic steroid is administered at a concentration of about 0.01 to 10.0 weight percent.

5. The method of claim 4 wherein the angiostatic steroid is administered at a concentration of about 0.1–5.0 weight percent.

* * * * *

UNITED STATES PATENT AND TRADEMARK OFFICE
CERTIFICATE OF CORRECTION

PATENT NO.    : 5,770,592
DATED         : June 23, 1998
INVENTOR(S)   : Abbot F. Clark It is certified that error appears in the above-identified patent and that said Letters Patent is hereby corrected as shown below:

Column 6,
Line 54, Claim 1 should also include the compound in Claim 2 -- [4,9(11)-Pregnadien-17a,21-diol-3,20-dione-21-acetate,] --

Signed and Sealed this

Twenty-seventh Day of May, 2003

JAMES E. ROGAN
*Director of the United States Patent and Trademark Office*